(12) United States Patent
Sizer et al.

(10) Patent No.: US 9,414,619 B2
(45) Date of Patent: Aug. 16, 2016

(54) LIQUID NUTRITIONAL FORMULA FOR PHENYLKETONURIA PATIENTS

(71) Applicant: Cambrooke Therapeutics, Inc., Ayer, MA (US)

(72) Inventors: Charles E. Sizer, Lincoln, MA (US); Leah Alea, Southborough, MA (US); Kurt Olson, Arlington, MA (US)

(73) Assignee: Cambrooke Therapeutics, Inc., Ayer, MA (US)

( * ) Notice: Subject to any disclaimer, the term of this patent is extended or adjusted under 35 U.S.C. 154(b) by 0 days.

(21) Appl. No.: 14/616,527

(22) Filed: Feb. 6, 2015

(65) Prior Publication Data
US 2015/0216213 A1    Aug. 6, 2015

Related U.S. Application Data

(60) Provisional application No. 61/938,653, filed on Feb. 11, 2014, provisional application No. 61/936,868, filed on Feb. 6, 2014.

(51) Int. Cl.
*A23L 1/305* (2006.01)
*A23L 1/29* (2006.01)
*A23L 1/302* (2006.01)
*A23L 1/303* (2006.01)
*A23L 1/304* (2006.01)

(52) U.S. Cl.
CPC ............... *A23L 1/296* (2013.01); *A23L 1/302* (2013.01); *A23L 1/303* (2013.01); *A23L 1/304* (2013.01); *A23L 1/3051* (2013.01)

(58) Field of Classification Search
CPC ..... A23L 1/296; A23L 1/3051; A23V 2002/00
USPC ............ 426/72, 73, 311, 648, 656, 657, 601, 426/603, 801
See application file for complete search history.

(56) References Cited

U.S. PATENT DOCUMENTS

| 5,587,399 A * | 12/1996 | Acosta ................... A23L 1/296 424/601 |
| 8,604,168 B2 | 12/2013 | Ney et al. |
| 2010/0317562 A1* | 12/2010 | Paolella ............... A23D 7/0053 514/1.1 |
| 2013/0196024 A1 | 8/2013 | Ney et al. |
| 2014/0248414 A1 | 9/2014 | Ney et al. |

FOREIGN PATENT DOCUMENTS

WO    WO 2014/171813 A1    10/2014

* cited by examiner

*Primary Examiner* — Helen F Heggestad
(74) *Attorney, Agent, or Firm* — Wolf, Greenfield & Sacks, P.C.

(57) ABSTRACT

This is a process to make a shelf-stable, liquid, ready-to-drink, aseptic nutritional formula for the treatment of PKU, tyrosinemia or other errors of metabolism. The liquid nutritional formula has caseino-glyco-macropeptide as the primary protein source and complementary essential amino acids to complete the requirement profile. The beverage also includes vitamins and minerals sufficient to meet daily requirements. When used as a complete diet, the nutritional formula includes a carbohydrate source and a fat source. The nutritional formula has a pleasant taste.

11 Claims, 5 Drawing Sheets

Fig. 2

INGREDIENTS
Water, sucrose, whey protein isolate, vitamin and mineral blend (dicalcium phosphate, calcium lactate, dipotassium phosphate, choline bitartrate, magnesium citrate, sodium ascorbate and ascorbic acid, ferrous sulfate, zinc sulfate, niacinamide, vitamin E dl-alpha-tocopheryl acetate, calcium d-pantothenate, manganese sulfate, vitamin A palmitate, vitamin B6 pyridoxine, riboflavin, thiamin hydrochloride, copper gluconate, folic acid, potassium iodide, vitamin K 1 phytonadione, sodium selenite, sodium molybdate, chromium chloride, biotin, vitamin D3 cholecalciferol, vitamin B12 cyanocobalamin), food starch modified, leucine, maltodextrin, cocoa butter, canola oil, arginine, tyrosine, cellulose gel and carboxymethylcellulose sodium, natural flavors (maltodextrin, natural flavors, acacia gum and propylene glycol), histidine, sodium hexametaphosphate, tryptophan, natural color (fruit juice, water, maltodextrin, sansgrenum), acesulfame potassium, sodium stearoyl lactylate, salt, sucralose.
Contains milk, soy and corn.

PREPARATION
Ready to drink.

STORAGE
Store in cool, dry place.

GLYTACTIN RTD 3-12 UNFLAVORED

INGREDIENTS
Water, trehalose, whey protein isolate, sucrose, vitamin and mineral blend (dicalcium phosphate, calcium lactate, dipotassium phosphate, choline bitartrate, magnesium citrate, sodium ascorbate and ascorbic acid, ferrous sulfate, niacinamide, zinc sulfate, vitamin E dl-alpha-tocopheryl acetate, calcium d-pantothenate, manganese sulfate, vitamin A palmitate, vitamin B6 pyridoxine, riboflavin, thiamin hydrochloride, copper gluconate, folic acid, potassium iodide, vitamin K1 phytonadione, sodium selenite, sodium molybdate, chromium chloride, vitamin D3 cholecalciferol, biotin, vitamin B12 cyanocobalamin), maltodextrin, leucine, food starch modified, cocoa butter, canola oil, cellulose gel and carboxymethylcellulose sodium, arginine, tyrosine, natural flavor (propylene glycol, ethyl alcohol, water, polysorbate 80, potassium sorbate), sodium hexametaphosphate, histidine, tryptophan, carrageenan, sodium stearoyl lactylate. Contains milk, soy and corn.

PREPARATION
Ready to drink.

STORAGE
Store in cool, dry place.

LIQUID NUTRITIONAL FORMULA FOR PHENYLKETONURIA PATIENTS

RELATED APPLICATIONS

This application claims the benefit of the filing date of U.S. provisional patent application 61/936,868, filed on Feb. 6, 2014 and U.S. provisional patent application 61/938,653, filed Feb. 11, 2014. The entire teachings and contents of the referenced provisional application are incorporated herein by reference

BACKGROUND

Phenylketonuria (PKU) is an inherited metabolic error that results in a toxic build-up of phenylalanine (Phe) in the brain and plasma. Infants are screened at birth to determine if they have the genetic defect responsible for PKU. If an infant is diagnosed with the condition, treatment must be initiated immediately, if there is to be a positive outcome. If PKU is undetected or untreated, the nervous system will suffer severe, irreversible damage and the individual will become severely mentally handicapped. Infants diagnosed with PKU must consume a low phenylalanine diet for life to avoid being affected. The original treatment for this disorder was simply to restrict protein in the diet. This fell far short of what was needed. Berry (1980) found that supplementing the diet with valine, isoleucine and leucine provided a method for improving outcome.

Subsequently, the PKU diets were composed of foods low in protein (and Phe) supplemented with a formula to provide complete nutrition, including amino acids, carbohydrate, fat and essential vitamin and minerals. Because there were no sources of intact protein that did not contain phenylalanine, purified amino acids were provided in lieu of protein (Brown et al 1992, Acosta et al 2002). Purified amino acid diets have an unpleasant taste because many of the free amino acids provide potent gustatory stimulation. In an effort to minimize the off-flavor notes of amino acid diets, Schweikhardt et al (1995) developed a dragee or capsule. Buist and Prince (1995) formulated a less objectionable mixture of amino acids which had less sensory impact.

Compliance is a concern for those with PKU and additional approaches to making palatable and nutritious foods suitable for those with PKU are needed.

SUMMARY

Described herein is a nutritional formula (also referred to as a nutritional formulation) that has a balanced amino acid profile suitable for therapy for individuals who have phenylketonuria (PKU), including complete, peptide-based, ready-to-drink nutritional formulas, such as shelf-stable, ready-to-drink (liquid), nutritional formulas that have a balanced amino acid profile and are suitable therapy for patients suffering from phenylketonuria. In some embodiments, the formula is produced under aseptic conditions. Alternatively, the formula is canned (placed in containers that are hermetically sealed and sterilized, such as by heat). Nutritional formulas that have a balanced amino acid profile suitable for therapy for individuals who have PKU described herein, are low in phenylalanine, have low osmolality and have an acceptable taste.

The nutritional formula comprises: (a) a protein source that comprises (i) caseino-glyco-macropeptide (cGMP) and (ii) complementary essential amino acids which are a mixture of tyrosine, arginine, tryptophan, leucine and histidine and, in combination, provide a balanced amino acid profile that includes an excess of tyrosine; (h) a carbohydrate source, which typically includes non-reducing sugars to minimize/reduce browning potential; (c) a fat (lipid/oil) source; and (d) vitamins and minerals in sufficient quantities to meet the daily requirements for each. In addition, the nutritional formulation typically, but optionally, includes flavors, which can be natural or artificial or a combination of both; coloring agents, which can be natural or artificial or a combination of both; sweetener, which can be natural or artificial or a combination of both; gelling agents, thickening agents, stabilizing agents, sequestrants, emulsifiers or a combination of two or more of gelling agents, thickening agents, stabilizing agents, sequestrants, emulsifiers, each of which can be natural or artificial or a combination of both.

In some embodiments, the protein source provides 10-80% of the energy of the nutritional formula. In some embodiments, the protein source provides 15-35% or 15% to 40% of the energy of the nutritional formula. In some embodiments, the protein source provides 20-80% of the energy of the nutritional formula. In some embodiments, the protein source provides 30-60% of the energy of the nutritional formula. In some embodiments, the protein source provides 40-50% of the energy of the nutritional formula. In some embodiments, the fat source provides 10-80% of the energy of the nutritional formula. In some embodiments, the fat source provides 20-80% of the energy of the nutritional formula. In some embodiments, the fat source provides 30-60% of the energy of the nutritional formula. In some embodiments, the fat source provides 40-50% of the energy of the nutritional formula. In some embodiments, the carbohydrate source provides 10-100% of the energy of the nutritional formula. In some embodiments, the carbohydrate source provides 20-80% of the energy of the nutritional formula. In some embodiments, the carbohydrate source provides 30-60% of the energy of the nutritional formula. In some embodiments, the carbohydrate source provides 40-50% of the energy of the nutritional formula. In some embodiments, the protein source provides 20-35% of the energy of the nutritional formula, the fat source provides 20% to 30% of the energy of the nutritional formula, and the carbohydrate source provides 40% to 60% of the energy of the nutritional formula.

In specific embodiments, the nutritional formula comprises components as shown in Table 1. In specific embodiments, the nutritional formula comprises modified starch, such as octenyl succinate starch or other modified starch that interferes with fat in the formula interacting with protein in the formula, such as by binding of the octenyl moiety of the starch to fat globules; binding of the modified starch to fat interferes (totally or partially) with interaction with proteins by steric hindrance.

Figure 2:
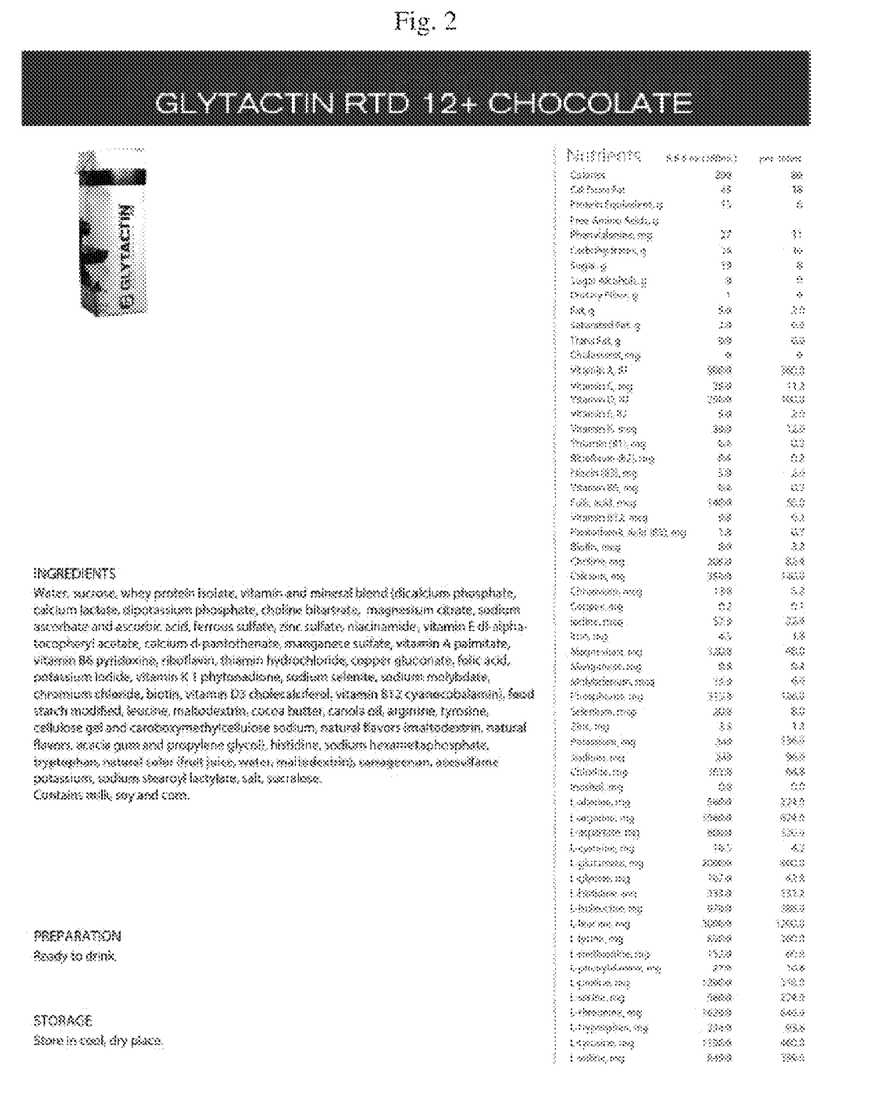
FIG. 2 shows a non-limiting embodiment of a liquid nutritional formula as described by the disclosure.
Figure 3:
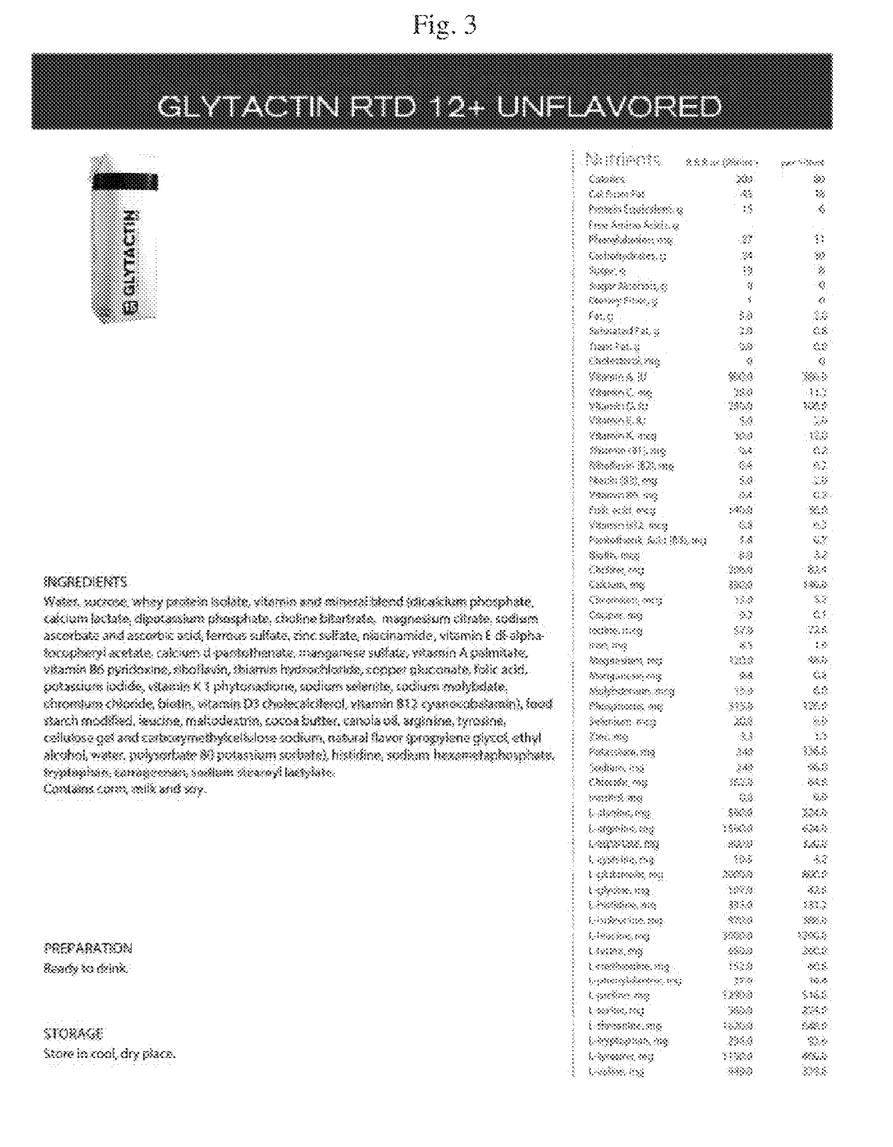
FIG. 3 shows a non-limiting embodiment of a liquid nutritional formula as described by the disclosure.
Figure 4:
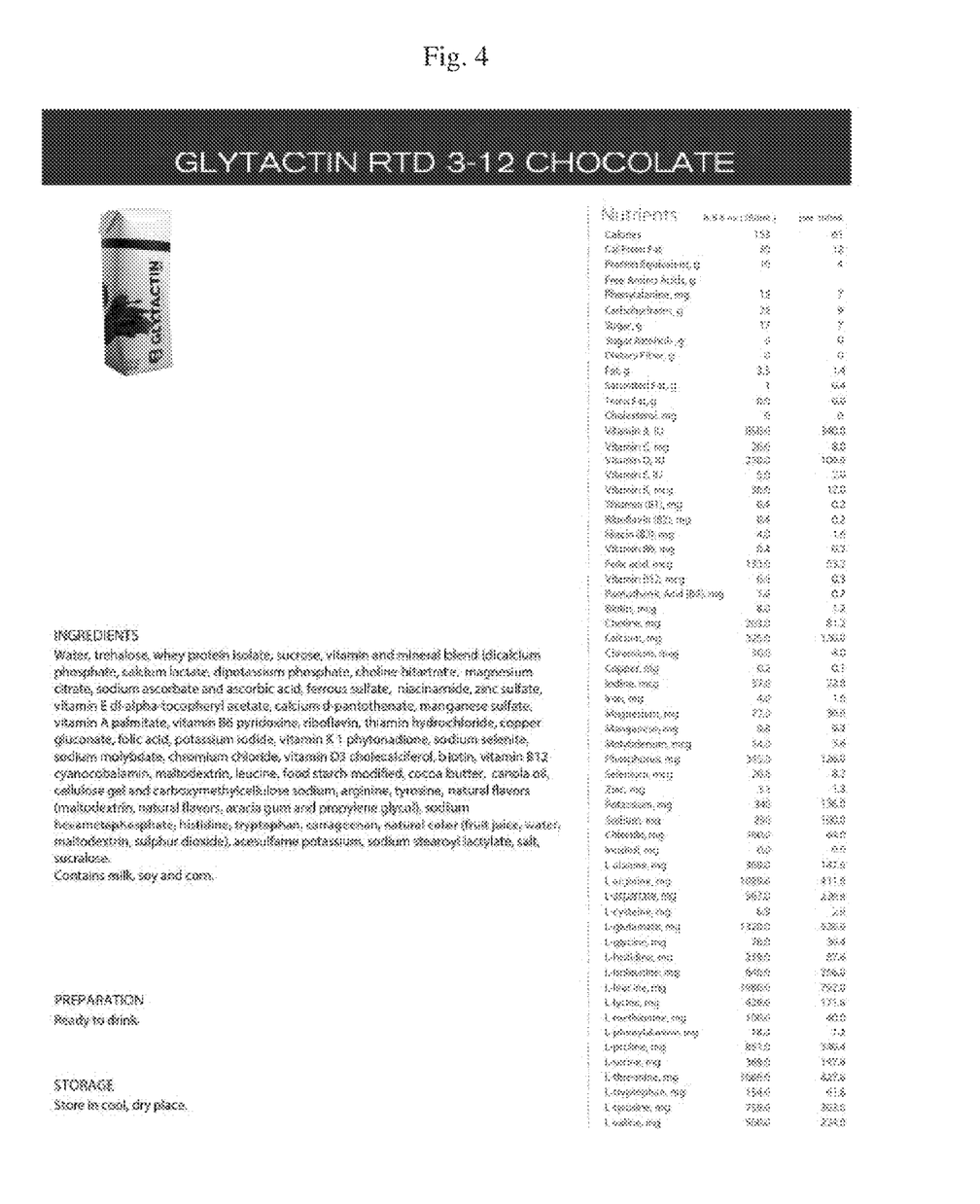
FIG. 4 shows a non-limiting embodiment of a liquid nutritional formula as described by the disclosure.
Figure 5:
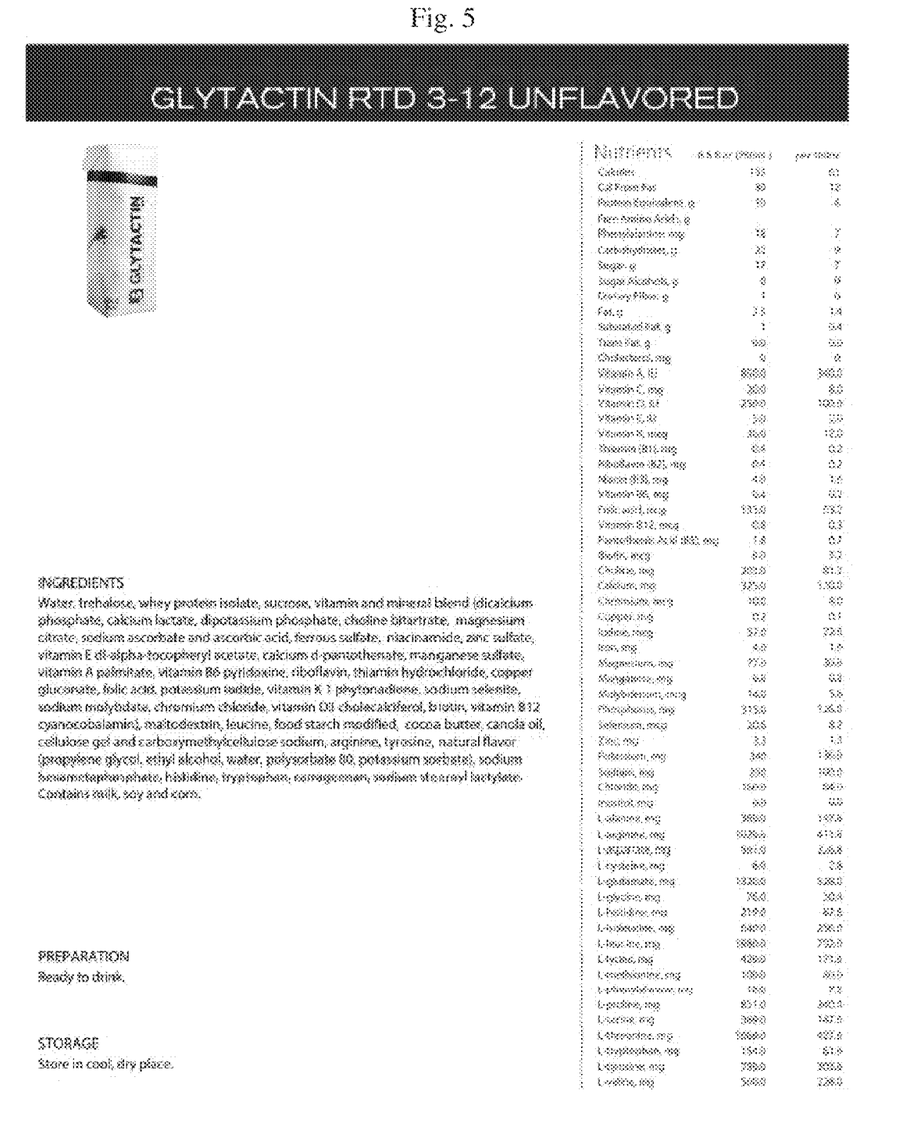
FIG. 5 shows a non-limiting embodiment of a liquid nutritional formula as described by the disclosure.

In further specific embodiments, nutritional formulas comprise (a) a protein source that comprises (i) caseino-glyco-macropeptide (cGMP) and (ii) complementary essential amino acids which are a mixture of tyrosine, arginine, tryptophan, leucine and histidine and, in combination, provide a balanced amino acid profile that includes an excess of tyrosine; (b) a carbohydrate source, which typically includes non-reducing sugars to minimize/reduce browning potential; (c) a fat (lipid/oil) source; and (d) vitamins and minerals in amounts and forms to provide, per 100 ml or per 250 ml (8.5 fluid ounces) the components as listed in FIG. 2, FIG. 3, FIG. 4 or FIG. 5.

The amount of caseino-glyco-macropeptide (cGMP) in the formulations can be varied, as needed. In some embodiments, the formulation includes from about 1 g caseino-glyco-macropeptide (cGMP). per 250 mL formulation to about 100 g caseino-glyco-macropeptide (cGMP) per 250 mL formulation. In some embodiments, the formulation includes from about 5 g caseino-glyco-macropeptide (cGMP) per 250 mL formulation to about 80 g caseino-glyco-macropeptide (cGMP) per 250 mL formulation. In some embodiments, the formulation includes from about 10 g caseino-glyco-macropeptide per 250 mL formulation to about 70 g caseino-glyco-macropeptide per 250 mL formulation. In some embodiments, the formulation includes from about 20 g caseino-glyco-macropeptide per 250 mL formulation to about 60 g caseino-glyco-macropeptide per 250 mL formulation. In some embodiments, the formulation provides from about 20 g caseino-glyco-macropeptide per 250 mL formulation to about 50 g caseino-glyco-macropeptide per 250 mL formulation.

The amount of each complementary essential amino acid in the formulations can also be varied, as needed. In some embodiments, the formulation includes from about 0.5 g of each complementary essential amino acid per 250 mL formulation to about 2 g of each complementary essential amino acid per 250 mL formulation. In some embodiments, the formulation provides from about 1 g of each complementary essential amino acid per 250 mL formulation to about 5 g of each complementary essential amino acid per 250 mL formulation. In some embodiments, the formulation provides from about 2 g of each complementary essential amino acid per 250 mL formulation to about 10 g of each complementary essential amino acid per 250 mL formulation. In some embodiments, the formulation provides from about 3 g of each complementary essential amino acid per 250 mL formulation to about 6 g of each complementary essential amino acid per 250 mL formulation.

In some aspects, the disclosure contemplates the amount of each complementary essential amino acid present in the formulations described herein relative to the amount of protein equivalent (PE) present in the formulations. In some embodiments, formulation provides from about 1 to about 500 mg per 1 gm of PE of each complementary essential amino acid. In some embodiments, formulation provides from about 10 to about 250 mg per 1 gm of PE of each complementary essential amino acid. In some embodiments, formulation provides from about 20 to about 100 mg per 1 gm of PE of each complementary essential amino acid. In some embodiments, formulation provides from about 50 to about 100 mg per 1 gm of PE of each complementary essential amino acid. In some embodiments, formulation provides from about 10 to about 50 mg per 1 gm of PE of each complementary essential amino acid.

The amount of carbohydrate source in the formulations described herein can also be varied, as needed. In some embodiments, the formulation includes from about 1 g carbohydrate source per 250 mL formulation to about 100 g carbohydrate source per 250 mL formulation. In some embodiments, the formulation provides from about 5 g carbohydrate source per 250 mL formulation to about 80 g carbohydrate source per 250 mL formulation. In some embodiments, the formulation provides from about 10 g carbohydrate source per 250 mL formulation to about 70 g carbohydrate source per 250 mL formulation. In some embodiments, the formulation provides from about 20 g carbohydrate source per 250 mL formulation to about 60 g carbohydrate source per 250 mL formulation. In some embodiments, the formulation provides from about 20 g carbohydrate source per 250 mL formulation to about 50 g carbohydrate source per 250 mL formulation.

The amount of fat (lipid/oil) source in the formulations described herein can also be varied, as needed. In some embodiments, the formulation includes from about 1 g fat (lipid/oil) source per 250 mL formulation to about 20 g fat (lipid/oil) source per 250 mL formulation. In some embodiments, the formulation provides from about 5 g fat (lipid/oil) source per 250 mL formulation to about 15 g fat (lipid/oil) source per 250 mL formulation. In some embodiments, the formulation provides from about 8 g fat (lipid/oil) source per 250 mL formulation to about 12 g fat (lipid/oil) source per 250 mL formulation.

The amount of each vitamin and each mineral source in the formulations described herein can be varied, as needed. In some embodiments, the formulation provides from about 0.01 g of each vitamin and each mineral source per 250 mL formulation to about 30 g of each vitamin and each mineral source per 250 mL formulation. In some embodiments, the formulation provides from about 0.05 g of each vitamin and each mineral source per 250 mL formulation to about 1 g of each vitamin and each mineral source per 250 mL formulation. In some embodiments, the formulation provides from about 0.5 g of each vitamin and each mineral source per 250 mL formulation to about 5 g of each vitamin and each mineral source per 250 mL formulation. In some embodiments, the formulation provides from about 2 g of each vitamin and each mineral source per 250 mL formulation to about 10 g of each vitamin and each mineral source per 250 mL formulation. In some embodiments, the formulation provides from about 5 g of each vitamin and each mineral source per 250 mL formulation to about 30 g of each vitamin and each mineral source per 250 mL formulation.

The formulation described herein is produced, using methods such as those also described herein, in such a manner that tyrosine does not precipitate even when included at levels in excess of its water solubility. The formulation is an emulsion in which tyrosine is contained in the lipid fraction.

Without wishing to be bound by theory, the charge interaction is reduced by steric hindrance provided by an octenyl succinate starch. The protein/lipid mixture forms a stable thixotropic gel whose viscosity can be precisely adjusted to suspend undissolved components of the mixture (combination). Transition ions in the formulation are ionically bound to reduce their precipitation and contribute to shelf stability.

BRIEF DESCRIPTION OF THE DRAWINGS

FIG. 1 is a schematic representation of the method by which nutritional formulas are produced.

DETAILED DESCRIPTION

Dietary compliance is the primary issue for PKU patients on amino acid formula, particularly those emerging from childhood. Schuett, V. E.; 1990; (DHHS Publication No HRS-MCH-89-5), reported that more >40% of PKU patients in the US, eight years or older, are not compliant with their diet. The high osmolality, bitterness of amino acids and metallic taste contributed by other components discourage formula consumption. There have been many attempts to improve acceptance of foods and beverages for those with PKU, such as making dry formulae that include caseino glycomacropeptide in combination with amino acids encapsulated to reduce their unpleasant flavor. (Ballevre et al. 2003). Although it might have a pleasant flavor, a powdered formula may not be convenient for a person on the go.

Ready-to-drink, shelf-stable formulae, such as beverages, pose particular challenges, at least in part because the components essential for complete sustenance components must be incorporated into or combined to produce the nutritional formula in such a way that they remain dissolved, suspended or otherwise retained in the formula (beverage). This is a challenge because each ingredient in the nutritional formula has unique requirements for making it stable. Particularly difficult to incorporate is the caseino-glycomacro-peptide, which contains sialic acid attached to an amino acid residue on the chain. This sialic acid reduces the isoelectric point of the peptide as a function of the fraction of sites occupied by sialic acid. Thus, the isoelectric point can change as the peptide is being processed. Peptides are not soluble at or near their isoelectric pH and tend to precipitate or gel. Described herein is a method by which nutritional formulas described are made, with the result that the formula is ready-to-drink and shelf-stable.

Formula Preparation

Nutritional formula preparation can be carried out using the method represented schematically in FIG. 1. Kitting of ingredients is carried out as indicated: Kitting of dry ingredients, to produce a dry ingredient mixture is prepared by kitting together dry ingredients without sodium hexametaphosphate (SHMP) or mineral blend; kitting together of SHMP, $CuSO_4$, $FeSO_4$ and, as needed, other minerals; and kitting of ingredients for oil incorporation. The SHMP and minerals are mixed in water separately. Ingredients for oil incorporation are heated and incorporated together. These include tyrosine, OSS, SSL, cocoa butter, vegetable oil and other oil-soluble ingredients. They are subject to high shear and homogenization to produce an emulsion. The resulting three combinations (see FIG. 1) are combined with water, as shown in FIG. 1 and subjected to the conditions shown, beginning with the step Sequentially Add to High Shear Blender. As represented, (1) water, GMP, amino acids, vitamins and other dry ingredients are added or introduced into a metered volume of water to produce a first mixture; (2) SHMP, minerals and water are kitted together and added to the result of (1); (3) the emulsion produced as shown in FIG. 1 is incorporated into the result of (1) and (2) and Vitamin C is added to the resulting product, which is subjected to UHT process at about 140° C. for a short time (e.g., 5-6 seconds). The resulting formula is stored in an aseptic tank and packaged, such as aseptically. Alternatively, the nutritional formula is packaged by canning. In some embodiments, the dry ingredients include caseino glycomacropeptides (GMP), amino acids, and vitamins.

SHMP is combined with minerals, such as a metal fortification mixture, which comprises at least one type of metallic ions to produce a SHMP-minerals in water (SHMP-metal mixture). In some embodiments, metal fortification mixture comprises two or more types of metallic ions. In some embodiments, the metallic ions is copper (e.g., $Cu^{2+}$) and/or iron (e.g., $Fe^{2+}$). In some embodiments, the metallic ions are from sources such as $CuSO_4$ and/or $FeSO_4$.

An emulsion is prepared by combining and heating oil ingredients, which includes tyrosine, modified starch, sodium stearoyl lactylate (SSL), oils such as cocoa butter and vegetable oil, and other oil soluble ingredients. The modified starch used herein is an amphiphilic starch, which is hydrophilic and hydrophobic in nature. The modified starch is used to bind to fat to prevent the fat from interacting with the proteins by steric hindrance. For example, a normally hydrophilic starch is modified to incorporate hydrophobic moieties such as octenyl groups which binds to fats. The resulting modified starch has an amphiphilic nature and thus surface active properties which are useful in stabilizing oil/water emulsions. In some embodiments, the modified starch is octenyl succinate starch (OSS) or another amphiphilic starch. The hydrophobic octenyl moiety binds the fats in the emulsion assuring that the starch remains attached to the fat globule, preventing the fats from interacting with the proteins by steric hindrance.

The heated and combined oil ingredients are then added to a mixer, such as a high shear mixer, with water and are homogenized to form an emulsion. In some embodiments, the oil ingredients are homogenized with water at about 60-80° C. and about 400 psi to about 3000 psi. In one embodiment, the oil ingredient are homogenized at about 70° C. and about 500 psi to about 2000 psi.

As shown, the mixtures are sequentially added to a blender such as a high shear blender: the dry ingredient mixture is mixed into metered volume of water, the fortified SHMP mixture is added, the emulsion is incorporated, and Vitamin C is added last. In some embodiments, the vitamin C is sodium ascorbate and/or ascorbic acid. The combined mixture is subjected to ultra-high temperature processing (UHT) at about 130-150° C. for about 4 to about 10 seconds. In one embodiment, the UHT process occurs at 140° C. for about 5 to about 6 seconds. The resulting formula is subsequently placed/stored in aseptic tank and then aseptically packaged.

Example

Dry ingredient mixture was prepared by kitting together the dry ingredients without sodium hexametaphosphate (SHMP), vitamins, or mineral. Table 1 below provides the weight of dry ingredients used. The dry ingredients are caseino glycomacropeptides (GMP), amino acids, vitamins, sugar, dextrin, natural flavoring products, natural food coloring, sodium chloride, cellulose gum, carrageenan, and sweeteners. In another step, SHMP is combined with a copper and iron fortification mixture. In another step, vitamins and minerals are mixed together in water to provide a vitamin and mineral fortification mixture. Subsequently, the SHMP with the copper and iron fortification mixture is mixed with the vitamin and mineral fortification mixture, thereby forming a metal/mineral fortified SHMP mixture.

In a separate step, an emulsion is prepared by combining and heating oil ingredients, which includes L-tyrosine, octenyl succinate modified starch (OSS), sodium stearoyl lactylate (SSL), cocoa butter, vegetable oil. The heated and combined oil ingredients are then added to a high shear mixer with water and are homogenized to form an emulsion at about 70° C. and about 500 psi to about 2000 psi.

The foregoing mixtures are then sequentially added to a blender such as a high shear blender in the following order: the dry ingredient mixture is mixed into metered volume of water, the fortified SHMP mixture is added, the emulsion is incorporated, and Vitamin C (sodium ascorbate and ascorbic acid) is added last. Table 1 below provides the amounts of each ingredient used to prepare the formula. The combined mixture is subjected to ultra-high temperature processing (UHT) at about 140° C. for about 5 to about 6 seconds The resulting formula is subsequently stored in aseptic tank and then aseptically packaged using Prisma Packages.

TABLE 1

Glytactin RTD chocolate 12+
Number of Servings: 4
(266.2485 g per serving)/250 ml
Weight: 1064.9940 g

| | Quantity | Range | Units | % Weight | Total Weight (g) |
|---|---|---|---|---|---|
| Water | 793.05 | | Gram | 74.4652 | 793.05 |
| Caseino glycomacropeptides (GMP) | 45.87 | 30-50 | Gram | 4.3071 | 45.87 |
| copper and iron fortification | 0.66 | 0.462-0.858 | Gram | 0.062 | 0.66 |
| Vitamin and mineral fortification | 19.68 | 13.776-25.584 | Gram | 1.8479 | 19.68 |
| L-Arginine | 6.274 | 5.0192-7.5288 | Gram | 0.5891 | 6.274 |
| L-Histidine | 1.398 | 1.118-1.6956 | Gram | 0.1313 | 1.398 |
| L-Leucine | 11.2 | 8.96-13.44 | Gram | 1.0516 | 11.2 |
| L-Tryptophan | 0.849 | 0.6792-1.0188 | Gram | 0.0797 | 0.849 |
| Sugar | 70 | 59.5-80.5 | Gram | 6.5728 | 70 |
| dextrin sweetener | 10 | 8.5-11.5 | Gram | 0.939 | 10 |
| Emulsion (see below) | 95.07 | 80.810-109.33 | Gram | 8.9268 | 95.07 |
| Natural flavors | 3.5 | 2.975-4.025 | Gram | 0.3286 | 3 |
| Natural color | 0.5 | 0.425-0.575 | Gram | 0.0469 | 0.5 |
| sodium chloride | 0.1 | 0.085-0.115 | Gram | 0.0094 | 0.1 |
| sodium hexametaphosphate | 1.288 | 0.1-1.5 | Gram | 0.1209 | 1.288 |
| cellulose gum | 4.69 | 3.0-7.0 | Gram | 0.4404 | 4.69 |
| carrageenan | 0.373 | 0.1-0.6 | Gram | 0.035 | 0.373 |
| Sweetener, artificial, Acesulfame-K | 0.25 | 0.2125-0.2875 | Gram | 0.0235 | 0.25 |
| Sweetener, sucralose, granular | 0.02 | 0.017-0.023 | Gram | 0.0019 | 0.02 |
| Vitamin C, sodium ascorbate | 0.152 | 0.1292-0.1748 | Gram | 0.0143 | 0.152 |
| Vitamin C, ascorbic acid | 0.07 | 0.0595-0.0805 | Gram | 0.0066 | 0.07 |

Emulsion
Number of Servings: 1
(95.071 g per serving)
Weight: 95.0710 g

| | Quantity | | Units | % Weight | Total Weight (g) |
|---|---|---|---|---|---|
| L-Tyrosine | 5.617 | 4.383-6.7404 62-93 mg/gm PE | Gram | 5.9082 | 5.617 |
| octenyl succinate modified starch | 11.54 | 2.0-20 | Gram | 12.1383 | 11.54 |
| Water | 57.714 | 49.0569-66.3711 | Gram | 60.7062 | 57.714 |
| Oil, cocoa butter | 10 | 8.5-11.5 | Gram | 10.5185 | 10 |
| Oil, canola | 10 | 8.5-11.5 | Gram | 10.5185 | 10 |
| sodium stearoyl lactylate | 0.2 | 0.17-0.23 | Gram | 0.2104 | 0.2 |

What is claimed is:

1. A liquid nutritional formula suitable as a complete diet for phenylketonuria (PKU) comprising whey protein isolate, tyrosine, tryptophan, arginine, leucine, histidine, copper, iron, sodium hexametaphosphate (SHMP), and octenyl succinate starch (OSS), wherein the whey protein isolate consists of caseino-glycomacropeptide (cGMP).

2. The nutritional formula according to claim 1 in which the protein isolate provides 20-35% of the energy of the nutritional formula, fat provides 20% to 30% of the energy of the nutritional formula, and the carbohydrate source provides 40% to 60% of the energy of the nutritional formula.

3. The nutritional formula according to claim 1, comprising the following complementary amino acids per gram of protein equivalent (PE),

| | |
|---|---|
| Tyrosine (mg/gm PE) | 93 |
| Tryptophan (mg/gm PE) | 14 |
| Arginine (mg/gm PE) | 90 |
| Leucine (mg/gm PE) | 200 |
| Histidine (mg/gm PE) | 24. |

4. The liquid nutritional formula of claim 3, which is an emulsion.

5. A liquid nutritional formula comprising:

| | |
|---|---|
| Calories | 200 |
| Cal From Fat | 45 |
| Protein Equivalent, g | 15 |
| Carbohydrates, g | 24 |
| Sugar, g | 19 |
| Sugar Alcohols, g | 0 |
| Dietary Fiber, g | 1 |
| Fat, g | 5.0 |
| Saturated Fat, g | 2.0 |
| Trans Fat, g | 0.0 |
| Cholesterol, mg | 0 |
| Vitamin A, IU | 900.0 |
| Vitamin C, mg | 28.0 |

| | |
|---|---:|
| Vitamin D, IU | 250.0 |
| Vitamin E, IU | 5.0 |
| Vitamin K, mcg | 30.0 |
| Thiamin (B1), mg | 0.4 |
| Riboflavin (B2), mg | 0.4 |
| Niacin (B3), mg | 5.0 |
| Vitamin B6, mg | 0.4 |
| Folic acid, mcg | 140.0 |
| Vitamin B12, mcg | 0.8 |
| Pantothenic Acid (B5), mg | 1.8 |
| Biotin, mcg | 8.0 |
| Choline, mg | 206.0 |
| Calcium, mg | 350.0 |
| Chromium, mcg | 13.0 |
| Copper, mg | 0.2 |
| Iodine, mcg | 57.0 |
| Iron, mg | 4.5 |
| Magnesium, mg | 120.0 |
| Manganese, mg | 0.8 |
| Molybdenum, mcg | 15.0 |
| Phosphorus, mg | 315.0 |
| Selenium, mcg | 20.0 |
| Zinc, mg | 3.3 |
| Potassium, mg | 340 |
| Sodium, mg | 240 |
| Chloride, mg | 162.0 |
| Inositol, mg | 0.0 |
| L-alanine, mg | 560.0 |
| L-arginine, mg | 1560.0 |
| L-aspartate, mg | 800.0 |
| L-cysteine, mg | 10.5 |
| L-glutamate, mg | 2000.0 |
| L-glycine, mg | 107.0 |
| L-histidine, mg | 333.0 |
| L-isoleucine, mg | 970.0 |
| L-leucine, mg | 3000.0 |
| L-lysine, mg | 650.0 |
| L-methionine, mg | 152.0 |
| L-phenylalanine, mg | 27.0 |
| L-proline, mg | 1290.0 |
| L-serine, mg | 560.0 |
| L-threonine, mg | 1620.0 |
| L-tryptophan, mg | 234.0 |
| L-tyrosine, mg | 1150.0 |
| L-valine, mg | 849.0, |
| Calories | 200 |
| Cal From Fat | 45 |
| Protein Equivalent, g | 15 |
| Carbohydrates, g | 24 |
| Sugar, g | 19 |
| Sugar Alcohols, g | 0 |
| Dietary Fiber, g | 1 |
| Fat, g | 5.0 |
| Saturated Fat, g | 2.0 |
| Trans Fat, g | 0.0 |
| Cholesterol, mg | 0 |
| Vitamin A, IU | 900.0 |
| Vitamin C, mg | 28.0 |
| Vitamin D, IU | 250.0 |
| Vitamin E, IU | 5.0 |
| Vitamin K, mcg | 30.0 |
| Thiamin (B1), mg | 0.4 |
| Riboflavin (B2), mg | 0.4 |
| Niacin (B3), mg | 5.0 |
| Vitamin B6, mg | 0.4 |
| Folic acid, mcg | 140.0 |
| Vitamin B12, mcg | 0.8 |
| Pantothenic Acid (B5), mg | 1.8 |
| Biotin, mcg | 8.0 |
| Choline, mg | 206.0 |
| Calcium, mg | 350.0 |
| Chromium, mcg | 13.0 |
| Copper, mg | 0.2 |
| Iodine, mcg | 57.0 |
| Iron, mg | 4.5 |
| Magnesium, mg | 120.0 |
| Manganese, mg | 0.8 |
| Molybdenum, mcg | 15.0 |
| Phosphorus, mg | 315.0 |
| Selenium, mcg | 20.0 |
| Zinc, mg | 3.3 |
| Potassium, mg | 340 |
| Sodium, mg | 240 |
| Chloride, mg | 162.0 |
| Inositol, mg | 0.0 |
| L-alanine, mg | 560.0 |
| L-arginine, mg | 1560.0 |
| L-aspartate, mg | 800.0 |
| L-cysteine, mg | 10.5 |
| L-glutamate, mg | 2000.0 |
| L-glycine, mg | 107.0 |
| L-histidine, mg | 333.0 |
| L-isoleucine, mg | 970.0 |
| L-leucine, mg | 3000.0 |
| L-lysine, mg | 650.0 |
| L-methionine, mg | 152.0 |
| L-phenylalanine, mg | 27.0 |
| L-proline, mg | 1290.0 |
| L-serine, mg | 560.0 |
| L-threonine, mg | 1620.0 |
| L-tryptophan, mg | 234.0 |
| L-tyrosine, mg | 1150.0 |
| L-valine, mg | 849.0, |
| Calories | 153 |
| Cal From Fat | 30 |
| Protein Equivalent, g | 10 |
| Carbohydrates, g | 22 |
| Sugar, g | 17 |
| Sugar Alcohols, g | 0 |
| Dietary Fiber, g | 0 |
| Fat, g | 3.5 |
| Saturated Fat, g | 1 |
| Trans Fat, g | 0.0 |
| Cholesterol, mg | 0 |
| Vitamin A, IU | 850.0 |
| Vitamin C, mg | 20.0 |
| Vitamin D, IU | 250.0 |
| Vitamin E, IU | 5.0 |
| Vitamin K, mcg | 30.0 |
| Thiamin (B1), mg | 0.4 |
| Riboflavin (B2), mg | 0.4 |
| Niacin (B3), mg | 4.0 |
| Vitamin B6, mg | 0.4 |
| Folic acid, mcg | 133.0 |
| Vitamin B12, mcg | 0.8 |
| Pantothenic Acid (B5), mg | 1.8 |
| Biotin, mcg | 8.0 |
| Choline, mg | 203.0 |
| Calcium, mg | 325.0 |
| Chromium, mcg | 10.0 |
| Copper, mg | 0.2 |
| Iodine, mcg | 57.0 |
| Iron, mg | 4.0 |
| Magnesium, mg | 77.0 |
| Manganese, mg | 0.8 |
| Molybdenum, mcg | 14.0 |
| Phosphorus, mg | 315.0 |
| Selenium, mcg | 20.6 |
| Zinc, mg | 3.3 |
| Potassium, mg | 340 |
| Sodium, mg | 250 |
| Chloride, mg | 160.0 |
| Inositol, mg | 0.0 |
| L-alanine, mg | 369.0 |
| L-arginine, mg | 1029.6 |
| L-aspartate, mg | 567.0 |
| L-cysteine, mg | 6.9 |
| L-glutamate, mg | 1320.0 |
| L-glycine, mg | 76.0 |
| L-histidine, mg | 219.0 |
| L-isoleucine, mg | 640.0 |
| L-leucine, mg | 1980.0 |
| L-lysine, mg | 429.0 |
| L-methionine, mg | 100.0 |
| L-phenylalanine, mg | 18.0 |
| L-proline, mg | 851.0 |
| L-serine, mg | 369.0 |
| L-threonine, mg | 1069.0 |

-continued

| | |
|---|---|
| L-tryptophan, mg | 154.0 |
| L-tyrosine, mg | 759.0 |
| L-valine, mg | 560.0, |
| or | |
| Calories | 153 |
| Cal From Fat | 30 |
| Protein Equivalent, g | 10 |
| Carbohydrates, g | 22 |
| Sugar, g | 17 |
| Sugar Alcohols, g | 0 |
| Dietary Fiber, g | 1 |
| Fat, g | 3.5 |
| Saturated Fat, g | 1 |
| Trans Fat, g | 0.0 |
| Cholesterol, mg | 0 |
| Vitamin A, IU | 850.0 |
| Vitamin C, mg | 20.0 |
| Vitamin D, IU | 250.0 |
| Vitamin E, IU | 5.0 |
| Vitamin K, mcg | 30.0 |
| Thiamin (B1), mg | 0.4 |
| Riboflavin (B2), mg | 0.4 |
| Niacin (B3), mg | 4.0 |
| Vitamin B6, mg | 0.4 |
| Folic acid, mcg | 133.0 |
| Vitamin B12, mcg | 0.8 |
| Pantothenic Acid (B5), mg | 1.8 |
| Biotin, mcg | 8.0 |
| Choline, mg | 203.0 |
| Calcium, mg | 325.0 |
| Chromium, mcg | 10.0 |
| Copper, mg | 0.2 |
| Iodine, mcg | 57.0 |
| Iron, mg | 4.0 |
| Magnesium, mg | 77.0 |
| Manganese, mg | 0.8 |
| Molybdenum, mcg | 14.0 |
| Phosphorus, mg | 315.0 |
| Selenium, mcg | 20.6 |
| Zinc, mg | 3.3 |
| Potassium, mg | 340 |
| Sodium, mg | 250 |
| Chloride, mg | 160.0 |
| Inositol, mg | 0.0 |
| L-alanine, mg | 369.0 |
| L-arginine, mg | 1029.6 |
| L-aspartate, mg | 567.0 |
| L-cysteine, mg | 6.9 |
| L-glutamate, mg | 1320.0 |
| L-glycine, mg | 76.0 |
| L-histidine, mg | 219.0 |
| L-isoleucine, mg | 640.0 |
| L-leucine, mg | 1980.0 |
| L-lysine, mg | 429.0 |
| L-methionine, mg | 100.0 |
| L-phenylalanine, mg | 18.0 |
| L-proline, mg | 851.0 |
| L-serine, mg | 369.0 |
| L-threonine, mg | 1069.0 |
| L-tryptophan, mg | 154.0 |
| L-tyrosine, mg | 759.0 |
| L-valine, mg | 560.0 | per 250 mL of formula, wherein the Protein Equivalent comprises caseino-glycomacropeptide (cGMP), and wherein the formula comprises octenyl succinate starch (OSS) and sodium hexametaphosphate (SHMP).

6. A method of producing a nutritional formula suitable as a complete diet for phenylketonuria, the method comprising:
(a) introducing, caseino-glycomacropeptide (cGMP), amino acids, vitamins and dry ingredients into a metered volume of water to produce a first mixture;
(b) introducing sodium hexametaphosphate (SHMP) and sensitive minerals into a metered volume of water to produce a second mixture;
(c) combining the first mixture and the second mixture;
(d) combining an emulsion comprising tyrosine, octenyl succinate starch (OSS), sodium steroyl lactylate (SSL), cocoa butter, vegetable oil with the product of (c); and
(e) adding Vitamin C to the product of (d), thereby producing a nutritional formula.

7. The method of claim 6 further comprising subjecting the product of (e) to high-shear mixing or blending.

8. The method of claim 7, wherein the method further comprises the step of storing the nutritional formula under aseptic conditions.

9. The method of claim 7, wherein the method further comprises aseptically packaging the nutritional formula.

10. A liquid, nutritional formula suitable as a complete diet for phenylketonuria comprising:

| | |
|---|---|
| Calories | 200.00 |
| Cal from Fat | 45.00 |
| Protein Equivalent, g | 15.00 |
| Carbohydrates, g | 24.00 |
| Sugar, g | 19.00 |
| Sugar alcohols, g | 0.00 |
| Dietary Fiber, g | 1.00 |
| Fat, g | 5.00 |
| Saturated Fat, g | 2.00 |
| Trans Fat, g | 0.00 |
| Cholesterol, mg | 0.00 |
| Vitamin A, mg | 900.00 |
| Vitamin C, mg | 28.00 |
| Vitamin D, IU | 250.00 |
| Vitamin E, IU | 5.00 |
| Vitamin K, mcg | 30.00 |
| Thiamin (b1), mg | 0.40 |
| Riboflavin (B2), mg | 0.40 |
| Niacin (B3), mg | 5.00 |
| Vitamin B6, mg | 0.40 |
| Folic Acid, mcg | 140.00 |
| Vitamin B12, mcg | 0.80 |
| Pantothenic Acid (B5), mg | 1.80 |
| Biotin, mcg | 8.00 |
| Choline, mg | 206.00 |
| Calcium, mg | 350.00 |
| Chromium, mcg | 13.00 |
| Copper, mg | 0.20 |
| Iodine, mcg | 57.00 |
| Iron, mg | 4.50 |
| Magnesium, mg | 120.00 |
| Manganese, mg | 0.80 |
| Molybdenum, mcg | 15.00 |
| Phosphorus, mg | 315.00 |
| Selenium, mcg | 20.00 |
| Zinc, mg | 3.30 |
| Potassium, mg | 340.00 |
| Sodium, mg | 240.00 |
| Chloride, mg | 162.00 |
| Inositol, mg | 0.00 |
| L-alanine, mg | 560.00 |
| L-arginine, mg | 1560.00 |
| L-aspartate, mg | 800.00 |
| L-cysteine, mg | 10.50 |
| L-glutamate, mg | 2000.00 |
| L-glycine, mg | 107.00 |
| L-histidine, mg | 333.00 |
| L-isoleucine, mg | 970.00 |
| L-leucine, mg | 3000.00 |
| L-lysine, mg | 650.00 |
| L-methionine, mg | 152.00 |
| L-phenylalanine, mg | 27.00 |
| L-proline, mg | 1290.00 |
| L-serine, mg | 560.00 |
| L-threonine, mg | 1620.00 |
| L-tryptophan, mg | 234.00 |
| L-tyrosine, mg | 1150.00 |
| L-valine, mg | 849.00 | per 250 mL of formula, wherein the Protein Equivalent comprises caseino-glycomacropeptide (cGMP), and wherein the formula comprises octenyl succinate starch (OSS) and sodium hexametaphosphate (SHMP).

11. A liquid, nutritional formula suitable as a complete diet for phenylketonuria comprising:

| | |
|---|---:|
| Calories | 153.00 |
| Cal from Fat | 30.00 |
| Protein Equivalent, g | 10.00 |
| Carbohydrates, g | 22.00 |
| Sugar, g | 17.00 |
| Sugar alcohols, g | 0.00 |
| Dietary Fiber, g | 1.00 |
| Fat, g | 3.50 |
| Saturated Fat, g | 1.00 |
| Trans Fat, g | 0.00 |
| Cholesterol, mg | 0.00 |
| Vitamin A, mg | 850.00 |
| Vitamin C, mg | 20.00 |
| Vitamin D, IU | 250.00 |
| Vitamin E, IU | 5.00 |
| Vitamin K, mcg | 30.00 |
| Thiamin (b1), mg | 0.40 |
| Riboflavin (B2), mg | 0.40 |
| Niacin (B3), mg | 4.00 |
| Vitamin B6, mg | 0.40 |
| Folic Acid, mcg | 133.00 |
| Vitamin B12, mcg | 0.80 |
| Pantothenic Acid (B5), mg | 1.80 |
| Biotin, mcg | 8.00 |
| Choline, mg | 203.00 |
| Calcium, mg | 325.00 |
| Chromium, mcg | 10.00 |
| Copper, mg | 0.20 |
| Iodine, mcg | 57.00 |
| Iron, mg | 4.00 |
| Magnesium, mg | 77.00 |
| Manganese, mg | 0.80 |
| Molybdenum, mcg | 14.00 |
| Phosphorus, mg | 315.00 |
| Selenium, mcg | 20.60 |
| Zinc, mg | 3.30 |
| Potassium, mg | 340.00 |
| Sodium, mg | 250.00 |
| Chloride, mg | 160.00 |
| Inositol, mg | 0.00 |
| L-alanine, mg | 369.00 |
| L-arginine, mg | 1029.60 |
| L-aspartate, mg | 567.00 |
| L-cysteine, mg | 6.90 |
| L-glutamate, mg | 1320.00 |
| L-glycine, mg | 76.00 |
| L-histidine, mg | 219.00 |
| L-isoleucine, mg | 640.00 |
| L-leucine, mg | 1980.00 |
| L-lysine, mg | 429.00 |
| L-methionine, mg | 100.00 |
| L-phenylalanine, mg | 18.00 |
| L-proline, mg | 851.00 |
| L-serine, mg | 369.00 |
| L-threonine, mg | 1069.00 |
| L-tryptophan, mg | 154.00 |
| L-tyrosine, mg | 759.00 |
| L-valine, mg | 560.00 | per 250 mL of formula, wherein the Protein Equivalent comprises caseino-glycomacropeptide (cGMP), and wherein the formula comprises octenyl succinate starch (OSS) and sodium hexametaphosphate (SHMP).

* * * * *